United States Patent [19]

Lacoste et al.

[11] Patent Number: 5,278,154
[45] Date of Patent: Jan. 11, 1994

[54] NEW VANADIUM COMPLEXES

[75] Inventors: Jean-Michel Lacoste, Sevres; Jacques Duhault, Croissy sur Seine; Denis Ravel, Igny, all of France

[73] Assignee: Adir et Compagnie, Courbevoie, France

[21] Appl. No.: 999,169

[22] Filed: Dec. 31, 1992

Related U.S. Application Data

[62] Division of Ser. No. 909,107, Jul. 2, 1992.

[30] Foreign Application Priority Data

Jul. 3, 1991 [FR] France .................................. 91 08253

[51] Int. Cl.$^5$ .................. A61K 31/555; C07D 401/12; C07F 9/09
[52] U.S. Cl. .................................. 514/114; 514/188; 546/6
[58] Field of Search ....................... 546/6; 514/114, 188

[56] References Cited

PUBLICATIONS

Nakajima, Chem Letters 1986, p. 1483.
Farmer, Inorg. Chem. 13, p. 587 (1974).
Kolawole J. C. S. Dalton 1241 (1981).

*Primary Examiner*—Mark L. Berch
*Attorney, Agent, or Firm*—Gordon W. Hueschen

[57] ABSTRACT

Compounds of formula (I):

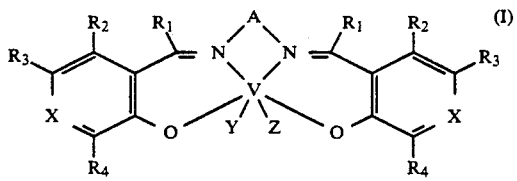

in which:

$R_1$ or $R_4$, which are identical or different, represent hydrogen or alkyl, $R_2$ represents hydrogenm or alkyl, hydroxymethyl, —$CH_2OPO(OH)_2$ or —$CH_2OPO(ONa)_2$, $R_3$ represents hydrogen, alkyl or hydroxyl or any one of the following groups:

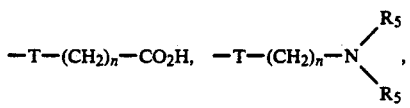

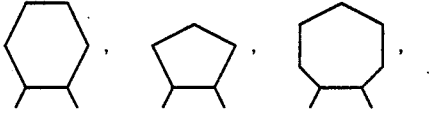

in which:

T represents oxygen or sulfur, n represents an integer between 1 and 4, $R_5$ represents hydrogen or alkyl, X represents nitrogen, CH or $CR'_3$ (in which $R'_3$ has the same meaning as $R_3$ except in the case where $R_3$ represents hydroxyl), A represents alkylene of formula —$(CH_2)_p$—in which p represents an integer between 2 and 4, optionally substituted by one or more linear or branched ($C_1$-$C_4$) alkyl, or any one of the following radicals:

Y and Z together form oxygen or simultaneously represent two hydroxyl and in this case, the compound of formula (I) is positively charged, their isomers as well as their addition salts with a pharmaceutically acceptable acid or base. Medicinal products.

9 Claims, No Drawings

NEW VANADIUM COMPLEXES

The present application is a division of our prior-filed copending application Ser. No. 07/909,107, filed Jul. 2, 1992, now allowed.

The present invention relates to new vanadium complexes. It has been found that orally-administered sodium vanadate possesses an antidiabetic efficacy (Science, 227, 1474, 1985). However, the diabetic state is characterized by a defect in the penetration of glucose into cells, which is due either to the absence of insulin (insulin-dependent diabetes), or to a reduced glucose tolerance or to a reduction in the efficacy of insulin at the peripheral tissue level (noninsulin-dependent diabetes), and which is linked to an increase in gycemia. The administration of insulin or insulin-like substances may correct these diabetic states. This is the case in particular for sodium vanadate as well as vanadium complexes described in Patents EP 305264 an JP 2-292217. These various complexes activate the transport of glucose and its metabolism. However, sodium vanadate exhibits a digestive intolerance which renders the absorption of the doses necessary for obtaining active blood concentrations difficult, in most cases.

The vanadium complexes described in the present invention possess, in addition to being new, the advantage of being better tolerated and less toxic, and they have demonstrated greater efficacy than the compounds described in the prior art, essentially due to a better bioavailability of the active biological entity.

The invention relates more particularly to new vanadium complexes of the formula (I):

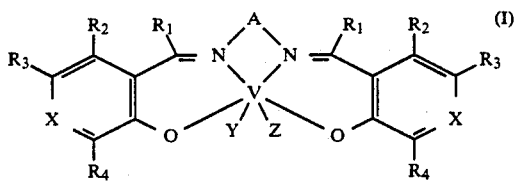

in which:

$R_1$ or $R_4$, which are identical or different, represent a hydrogen atom or a linear or branched ($C_1$-$C_6$) alkyl group, $R_2$ represents a hydrogen atom, a linear or branched ($C_1$-$C_6$) alkyl group, a hydroxymethyl group, a group —$CH_2OPO(OH)_2$ or group —$CH_2OPO(ONa)_2$, $R_3$ represents a hydrogen atom, a linear or branched ($C_1$-$C_6$) alkyl group, a hydroxyl group or any one of the following groups:

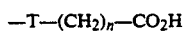

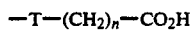

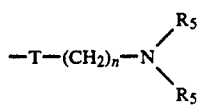

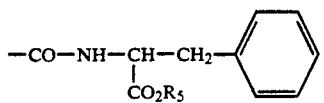

in which:

T represents an oxygen or sulfur atom, n represents an integer between 1 and 4, $R_5$ represents a hydrogen atom or a linear or branched ($C_1$-$C_6$) alkyl group, X represents a nitrogen atom, A represents an alkylene radical of formula —$(CH_2)_p$— in which p represents an integer between 2 and 4, optionally substituted by one or more linear or branched ($C_1$-$C_4$) alkyl groups, or any one of the following radicals:

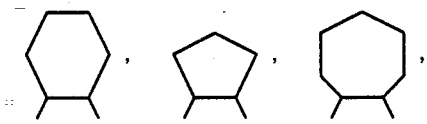

Y and Z together form an oxygen atom and or alternatively, simultaneously their isomers, enantiomers, diastereoisomers and epimers as well as their addition salts with a pharmaceutically, acceptable acid or base.

Among the pharmaceutically acceptable acids, hydrochloric, hydrobromic, sulfuric, phosphonic, acetic, trifluoroacetic, lactic, pyruvic, malonic, succinic, glutaric, fumaric, tartaric, maleic, citric, ascorbic, oxalic, methanesulfonic and camphoric acids and the like, may be mentioned with no limitation being implied.

Among the pharmaceutically acceptable bases, sodium hydroxide, potassium hydroxide, triethylamine and tert-butylamine and the like, may be mentioned with no limitation being implied.

The invention also extends to the process for preparing compounds of formula (I), wherein two equivalents of a compound of formula (II):

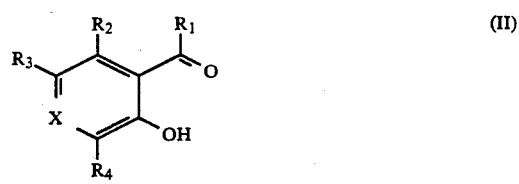

in which $R_1$, $R_2$, $R_3$ and $R_4$ have the same meaning as in the formula (I), are reacted with one equivalent of a compound of formula (III), under an inert atmosphere:

in which A has the same meaning as in the formula (I), to lead to the compound of formula (IV) whose isomers are optionally separated by a conventional separation technique, which compound:

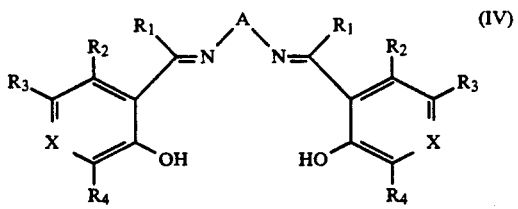

in which $R_1$, $R_2$, $R_3$, $R_4$, A and X have the same meaning as in the formula (I), is purified where appropriate by a conventional purification technique, and which compound is treated:

either with an aqueous solution of vanadyl sulfate pentahydrate in dichloromethane medium, or alternatively, after treating with sodium hydroxide, with an aqueous solution of vanadyl sulfate pentahydrate in tetrahydrofuran medium or alternatively with vanadyl sulfate in dimethylformamide medium, to lead to the complex of formula (I/a), which is a specific example of the compounds of formula (I) in which the vanadium has the oxidation number IV:

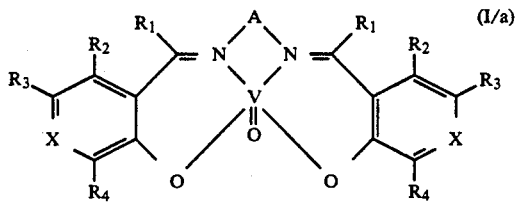

or with a solution of vanadyl sulfate in dimethylformamide in the presence of oxygen, according to the technique described by H. J. BIELIG et al., (Liebigs Ann. Chem., 580, 135, 1953) to lead to the complex of formula (I/b), which is a specific example of the compounds of formula (I),

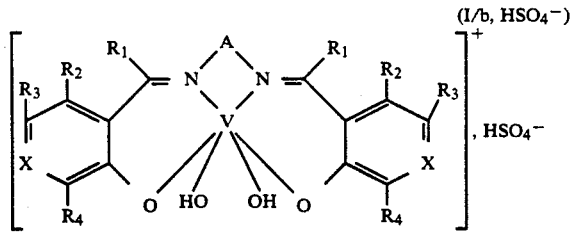

which compounds of formula (I/a) or (I/b) are purified, where appropriate, by a conventional purification technique and converted, if desired, to their addition salts with a pharmaceutically acceptable acid or base.

The compounds of the invention possess very useful pharmacological properties. They possess insulin-like activities not only in vitro but also in vivo. The results obtained both during the measurement of glucose metabolism and the capture of 2-deoxyglucose and during trials carried out on genetically insulin-resistant mice or on rats rendered diabetic by streptozotocin injection, show that the compounds of the invention can be used in the treatment of insulin-resistance states associated or unassociated with hyperglycemia and hyperinsulinemia such as type I and II diabetes, obesity and hypertension.

A favorable consequence of treatment using these compounds is the reduction in blood lipids which may contribute to the prevention of macroangiopathies.

The present invention also extends to the use of [N,N'-di(salicylidene)ethylenediamine]oxovanadium (IV) (described by P. Pfeiffer et al., J. für Praktische Chemie, 149, 217, 1937) for producing pharmaceutical compositions which are useful in the treatment of diabetes.

The subject of the present invention is also the pharmaceutical compositions containing as active ingredient, at least one compound of general formula (I) or one of its addition salts with a pharmaceutically acceptable acid, alone or in combination with one or more inert, nontoxic excipients or vehicles.

Among the pharmaceutical compositions according to the invention, those which are suitable for oral, parenteral or nasal administration, simple or sugared tablets, sublingual tablets, sachets, packets, gelatin capsules, sublingual preparations, troches, suppositories, creams, ointments, skin gels or aerosols may be more particularly mentioned.

The dosage varies according to the age and weight of the patient, the nature and severity of the condition as well as the route of administration. The administration may be oral, nasal, rectal or parenteral. It ranges generally between 100 mg and 1 g for a treatment in one or more doses per 24 hours.

The following examples illustrate the invention and do not imply any limitation.

Preparations A to E do not enable the compounds of the invention to be obtained but lead to intermediates which are useful during synthesis of the compounds of the invention.

Preparation A:
2-Hydroxy-4-[2-(dimethylamino)ethoxy]benzaldehyde

A mixture containing 0.8 mole of 2,4-dihydoxy-benzaldehyde, 0.8 mole of 2-chloro-1-dimethylaminoethane and 1.6 mole of potassium carbonate in 1200 ml of anhydrous methyl ethyl ketone is refluxed for 1 hour 30 minutes with stirring. After cooling, the precipitate formed is filtered and washed with methyl ethyl ketone. The filtrate is then evaporated and leads to a brown oil which is purified by chromatography of a silica column using a dichloromethane-methanol mixture (90/10) as eluting solvent. The expected product is then obtained after recrystallization from isopropanol.

Melting point: 82°–83° C.

| | Elemental microanalysis: | | |
|---|---|---|---|
| | C % | H % | N % |
| Calculated | 63.14 | 7.23 | 6.69 |
| Found | 63.24 | 7.15 | 6.58 |

Preparation B:
2-Hydroxy-5-[2-(dimethylamino)ethoxy]benzaldehyde

The expected product is obtained in the form of a pale yellow oil using the same procedure as that described in preparation A but replacing 2,4-dihydroxy-benzaldehyde with 2,5-dihydroxy benzaldehyde.

| | Elemental microanalysis: | | |
|---|---|---|---|
| | C % | H % | N % |
| Calculated | 63.14 | 7.23 | 6.69 |

| | Elemental microanalysis: | | |
|---|---|---|---|
| | C % | H % | N % |
| Found | 62.92 | 7.17 | 6.73 |

Preparation C:
2-Hydroxy-4-(ethoxycarbonylmethoxy)-benzaldehyde

By carrying out the procedure as in preparation A but replacing 2-chloro-1-dimethylaminoethane with ethyl bromoacetate and by refluxing the mixture for 3 hours, the expected product is obtained and purified by crystallization of the oily residue from toluene, leading to a white powder.

Melting point: 97°–99° C.

| | Elemental microanalysis: | |
|---|---|---|
| | C % | H % |
| Calculated | 58.93 | 5.39 |
| Found | 59.19 | 5.50 |

Preparation D:
N-(3-Formyl-4-hydroxybenzoyl)phenylalanine methyl ester 87 mmol of dicyclohexylcarbodiimide are added to a stirred suspension, cooled to 10° C., containing 80 mmol of 3-formyl-4-hydroxybenzoic acid (prepared according to H. WYMBERG, J. Am. Chem. Soc., 76, 4998, 1954) and 87 mmol of N-hydroxysuccinimide in 320 ml of chloroform. After re-equilibrating to room temperature, the mixture is kept stirring overnight. The precipitate is then filtered. The filtrate is cooled to 8° C. and treated dropwise, with stirring, with a suspension containing 160 mmol of phenylalanine methyl ester hydrochloride and 160 mmol of triethylamine in 100 ml of anhydrous dimethylformamide. The mixture is stirred for 3 hours at 20° C. and then for 5 hours at 50° C. After cooling and evaporation of the solvents, the residue is taken up in 400 ml of ethyl acetate. After washing this solution with 1N hydrochloric acid and then with water, the organic phase is dried and evaporated. The oily residue leads to the expected product by crystallization from toluene.

Melting point: 128°–129° C.

| | Elemental microanalysis: | | |
|---|---|---|---|
| | C % | H % | N % |
| Calculated | 66.05 | 5.23 | 4.28 |
| Found | 66.21 | 5.34 | 4.76 |

Preparation E:
N-(4-Formyl-3-hydroxybenzoyl)phenylalanine methyl ester

The expected product is obtained by carrying out the procedure as in preparation D but replacing 3-formyl-4-hydroxybenzoic acid with 4-formyl-3-hydroxybenzoic acid (prepared according to T. L. HULLAR et al., J. Med. Chem., 12, 420, 1968).

Melting point: 131°–133° C.

| | Elemental microanalysis: | | |
|---|---|---|---|
| | C % | H % | N % |
| Calculated | 66.05 | 5.23 | 4.28 |
| Found | 66.21 | 5.34 | 4.76 |

EXAMPLE 1:
[N,N'-Di-[4-(2-dimethylaminoethoxy)salicylidene]ethylenediamine]oxovanadium (IV)

STAGE A: N,N'-Di-[4-(2-dimethylaminoethoxy)salicylidene]ethylenediamine 25 mmol of ethylenediamine are added dropwise, under a nitrogen atmosphere, to a solution containing 50 mmol of the compound obtained in preparation A in 50 ml of anhydrous ethanol. The mixture is refluxed for one hour. After cooling and evaporation of the solvent, the expected product is obtained after recrystallization of the residue from cyclohexane.

Yield: 84%
Melting point: 92°–94° C.

| | Elemental microanalysis: | | |
|---|---|---|---|
| | C % | H % | N % |
| Calculated | 65.14 | 7.74 | 12.66 |
| Found | 65.00 | 7.72 | 12.62 |

STAGE B: [N,N'-Di-[4-(2-dimethylaminoethoxy)salicylidene]ethylenediamine]oxovanadium (IV)

A solution containing 14 mmol of vanadyl sulfate pentahydrate in 40 ml of distilled water is added, with stirring at room temperature, to a solution containing 14 mmol of the compound obtained in Stage A in 50 ml of dichloromethane. The mixture is stirred for 30 minutes and then decanted. The aqueous phase, which is green in color, is diluted with 50 ml of distilled water and then filtered. The filtrate is treated with triethylamine until a basic pH is obtained, accompanied by precipitation. The aqueous phase and the precipitate are extracted with dichloromethane. This organic phase is then washed with water, dried and then evaporated. The expected product is obtained by recrystallization of the solid residue from toluene.

Yield: 84%
Melting point: 190°–192° C.

| | Elemental microanalysis: | | | |
|---|---|---|---|---|
| | C % | H % | N % | V % |
| Calculated | 56.80 | 6.36 | 11.04 | 10.04 |
| Found | 56.60 | 6.33 | 10.97 | 10.26 |

The following examples were obtained using the same procedure as that described in Example 1.

EXAMPLE 2:
[N,N'-Di-[4-(2-dimethylaminoethoxy)salicylidene]propylenediamine]oxovanadium (IV)

STAGE A:
N,N'-Di-[4-(2-dimethylaminoethoxy)salicylidene]propylenediamine

This stage is identical to stage A of Example 1 but ethylenediamine is replaced by propylenediamine.

Yield: 82%

Melting point: 63°–65° C.

| | Elemental microanalysis: | | |
|---|---|---|---|
| | C % | H % | N % |
| Calculated | 65.77 | 7.95 | 12.27 |
| Found | 65.24 | 8.08 | 12.57 |

STAGE B: [N,N'-Di-[4-(2-dimethylaminoethoxy)salicylidene]propylenediamine]oxovanadium (IV)

This stage B is identical to stage B of Example 1.
Yield: 82%
Melting point: 208°–211° C.

| | Elemental microanalysis: | | |
|---|---|---|---|
| | C % | H % | N % |
| Calculated | 57.58 | 6.57 | 10.74 |
| Found | 57.31 | 6.45 | 10.81 |

EXAMPLE 3:[N,N'-Di-[4-(2-dimethylaminoethoxy)salicylidene](-trans-1,2-cyclohexane)diamine]oxovanadium (IV)

STAGE A: N,N'-Di-[4-(2-dimethylaminoethoxy)salicylidene]-(trans-1,2-cyclohexane)diamine The expected product is obtained in the form of an oil by carrying out the procedure as in stage A of Example 1 but replacing ethylenediamine with (trans-1,2-cyclohexane)diamine. Yield: 77%

| | Elemental microanalysis: | | |
|---|---|---|---|
| | C % | H % | N % |
| Calculated | 67.44 | 8.49 | 11.24 |
| Found | 67.33 | 8.57 | 11.05 |

STAGE B:
[N,N'-Di-[4-(2-dimethylaminoethoxy)salicylidene](-trans-1,2-cyclohexane)diamine]-oxovanadium (IV)

Stage B is identical to stage B of Example 1.
Yield: 80%
Melting point: 178°–182° C.

| | Elemental microanalysis: | | |
|---|---|---|---|
| | C % | H % | N % |
| Calculated | 59.89 | 6.82 | 9.98 |
| Found | 59.89 | 6.72 | 9.76 |

EXAMPLE 4:
[N,N'-Di-[5-(2-dimethylaminoethoxy)salicylidene]ethylenediamine]oxovanadium (IV)

STAGE A:
N,N'-Di-[5-(2-dimethylaminoethoxy)salicylidene]ethylenediamine

The expected product is obtained by carrying out the procedure as in stage A of Example 1 but using as starting product the compound obtained in preparation B in place of the compound obtained in preparation A.
Yield: 72%,
Melting point: 84°–86° C.

| | Elemental microanalysis: | | |
|---|---|---|---|
| | C % | H % | N % |
| Calculated | 65.14 | 7.74 | 12.66 |
| Found | 64.93 | 8.15 | 12.78 |

STAGE B:
[N,N'-Di-[5-(2-dimethylaminoethoxy)salicylidene]ethylenediamine]oxovanadium (IV)

Stage B is identical to stage B of Example 1.
Yield: 75%
Melting point: 180°–184° C.

| | Elemental microanalysis: | | |
|---|---|---|---|
| | C % | H % | N % |
| Calculated | 56.80 | 6.36 | 11.04 |
| Found | 56.75 | 6.22 | 11.02 |

EXAMPLE 5:
[N,N'-Di-(3,4,6-trimethyl-5-hydroxysalicylidene)ethylenediamine]oxovanadium (IV)

STAGE A:
N,N'-Di-(3,4,6-trimethyl-5-hydroxysalicylidene)ethylenediamine

The expected product is obtained by carrying out the procedure as in stage A of Example 1 but using as starting product 3,4,6-trimethyl-2,5-hydroxybenzaldehyde obtained as described by A. MAYER et al., (Helvetica Chem. Acta, XLVI (II), 67, 650, 1963) in place of the compound described in preparation A.
Yield: 86%
Melting point: 225°–229° C.

| | Elemental microanalysis: | | |
|---|---|---|---|
| | C % | H % | N % |
| Calculated | 68.73 | 7.34 | 7.29 |
| Found | 68.23 | 7.41 | 7.02 |

STAGE B:
[N,N'-Di-(3,4,6-trimethyl-5-hydroxysalicylidene)ethylenediamine]oxovanadium (IV)

Stage B is identical to stage B of Example 1.
Yield: 81%
Melting point: >250° C.

| | Elemental microanalysis: | | |
|---|---|---|---|
| | C % | H % | N % |
| Calculated | 58.80 | 5.83 | 6.23 |
| Found | 58.64 | 5.48 | 6.59 |

EXAMPLE 6:[N,N'-Di-[5-[(phenylalanine methyl ester)carbonyl]salicylidene]ethylenediamine]oxovanadium (IV)

STAGE A: N,N'-Di-[5-[(phenylalanine methyl ester)carbonyl]salicylidene]ethylenediamine The expected product is obtained by carrying out the procedure as in stage A of Example 1 but using as starting product the compound obtained in preparation D in place of the compound obtained in preparation A.

Yield: 70%.
Melting point: 186°–187° C.

| Elemental microanalysis: | | | |
|---|---|---|---|
| | C % | H % | N % |
| Calculated | 67.24 | 5.64 | 8.25 |
| Found | 66.99 | 5.69 | 8.40 |

STAGE B: [N,N'-Di-[5-[(phenylalanine methyl ester)carbonyl]salicylidene]ethylenediamine]oxovanadium (IV)

Stage B is identical to stage B of Example 1.
Yield: 64%
Melting point: 154°–162° C.

| Elemental microanalysis: | | | |
|---|---|---|---|
| | C % | H % | N % |
| Calculated | 61.37 | 4.88 | 7.53 |
| Found | 61.25 | 4.80 | 7.56 |

EXAMPLE 7: [N,N'-Di-[4-[(phenylalanine methyl ester)carbonyl]salicylidene]ethylenediamine]oxovanadium (IV)

STAGE A: N,N'-Di-[4-[(phenylalanine methyl ester)carbonyl]salicylidene]ethylenediamine The expected product is obtained by carrying out the procedure as in stage A of Example 1 but using as starting product the compound obtained in preparation E in place of the compound obtained in preparation A.
Yield: 72%
Melting point: 162°–166° C.

| Elemental microanalysis: | | | |
|---|---|---|---|
| | C % | H % | N % |
| Calculated | 67.24 | 5.64 | 8.25 |
| Found | 67.05 | 5.51 | 8.22 |

STAGE B: N,N'-Di-[4-[(phenylalanine methyl ester)carbonyl]salicylidene]ethylenediamine]-oxovanadium (IV)

Stage B is identical to stage B of Example 1.
Yield 56%.
Melting point: 252°–256° C.

| Elemental microanalysis: | | | |
|---|---|---|---|
| | C % | H % | N % |
| Calculated | 61.37 | 4.88 | 7.53 |
| Found | 60.52 | 4.81 | 7.59 |

EXAMPLE 8: [N,N'-(Bis-pyridoxal)ethylenediimine]oxovanadium (IV)

STAGE A: N,N'-(Bis-pyridoxal)ethylenediimine

The expected product is obtained as described in Patent EP-292761.

STAGE B: [N,N'-(Bis-pyridoxal)ethylenediimine]-oxovanadium (IV)

Stage B is identical to stage B of Example 1.
Yield: 82%
Melting point: >250° C.

| Elemental microanalysis: | | | |
|---|---|---|---|
| | C % | H % | N % |
| Calculated | 51.07 | 4.76 | 13.23 |
| Found | 50.77 | 4.87 | 13.23 |

EXAMPLE 9: [N,N'-Di-[4-(carboxymethyloxy)salicylidene]ethylenediamine]oxovanadium (IV), di-tertbutylamine salt

STAGE A: N,N'-Di-[4-(ethoxycarbonylmethyloxy)salicylidene]ethylenediamine

The expected product is obtained by carrying out the procedure as in stage A of Example 1 but using as starting product the compound obtained in preparation C in place of the compound obtained in preparation A.
Yield: 80%
Melting point: 104°–106° C.

| Elemental microanalysis: | | | |
|---|---|---|---|
| | C % | H % | N % |
| Calculated | 61.01 | 5.97 | 5.93 |
| Found | 60.87 | 6.05 | 5.85 |

STAGE B: [N,N'-Di-[4-(carboxymethyloxy)salicylidene]ethylenediamine]oxovanadium (IV), di-tertbutylamine salt 20 ml of 1N NaOH are added, at room temperature, to a suspension containing 16 mmol of the product obtained in stage A in 100 ml of a tetrahydrofuran/water mixture (50/50). After stirring for 4 hours, the tetrahydrofuran is evaporated; the residual aqueous phase is washed with dichloromethane and treated with a solution containing 10 mmol of vanadyl sulfate pentahydrate in 20 ml of distilled water. The reaction mixture is kept stirring at room temperature for omol of vanadyl tes and then acidified with 3N hydrochloric acid until a pH value of 3–4 is obtained. The precipitate formed is filtered, washed with water until neutral and dried.

The corresponding tert-butylamine salt is formed by stirring the precipitate formed in an aqueous solution of tert-butylamine and purified by recrystallization from a water/acetone mixture (30/70).
Yield: 53%.
Melting point: 235°–240° C.

| Elemental microanalysis: | | | |
|---|---|---|---|
| | C % | H % | N % |
| Calculated | 53.59 | 6.42 | 8.93 |
| Found | 53.55 | 6.17 | 8.28 |

EXAMPLE 10: [N,N'-Bis(5-pyridoxal phosphate)ethylenediimine]oxovanadium (IV), tetrasodium salt

STAGE A: N,N'-(bis-pyridoxal phosphate)ethylenediimine, tetrasodium salt

The expected product is obtained as described in Patent EP 290047.

STAGE B: N,N'-Bis[(5-pyridoxal phosphate)ethylenediimine]oxovanadium (IV), tetrasodium salt A solution containing 10 mmol of the product obtained in stage A in 20 ml of distilled water is treated at room temperature, with stirring, with a solution containing 10 mmol of vanadyl sulfate penta-hydrate in 15 ml of distilled water.

After stirring for one hour, the precipitate formed is filtered, dried and then taken up in 100 ml of water. The suspension is treated with 12 ml of 1N NaOH. The solution is filtered and evaporated. The expected product is obtained by recrystallization of the residue from a water/ethanol mixture (30/70).

Yield: 76%.
Melting point: >250° C.

| Elemental microanalysis: | | | |
|---|---|---|---|
| | C % | H % | N % |
| Calculated | 32.21 | 2.70 | 8.35 |
| Found | 32.55 | 3.79 | 7.85 |

PHARMACOLOGICAL STUDIES OF THE COMPOUNDS OF THE INVENTION

EXAMPLE 11: Insulin-like effects in vitro

Insulin-like effects of the compounds of the invention were studied in vitro on adipose tissue fragments by measuring the metabolism of carbon 14-labelled glucose and the capture of 2-deoxyglucose according to the techniques described by M. RODBELL (J. Biol. Chem., 239, 375, 1964) and by J. M. OLEFSKY (J. Clin. Invest., 56, 1499, 1975)

The results obtained with the compounds of the invention were compared with the response to insulin which represents $+100\%$ at $10^{-9}$M. The reference product used is sodium orthovanadate.

The results obtained at $10^{-4}$M are collated in the table below:

| Ex | Metabolism of labelled glucose | Capture of 2-deoxyglucose |
|---|---|---|
| Ex 1 | +43% | +78% |
| Ex 3 | +51% | +96% |
| Ex 4 | +56% | +113% |
| Sodium orthovanadate | +23% | +95% |

These results show that the metabolism of labelled glucose and the capture of 2-deoxyglucose by the adipose tissue are increased by the presence of insulin (+100%) or the compounds mentioned.

EXAMPLE 12: Hypoglycemic response in vivo

The hypoglycemic response was studied after oral administration of the compounds of the invention, after suspension in a 20% solution of Senegal gum, to rats rendered diabetic by the injection of streptozotocin (65 mg/kg) according to the technique described by A. JUNOD et al., (J. Clin. Invest., 48, 11, 2129, 1969).

The results, indicating the decrease in glycemia observed after 10 days of treatment with the compounds of the invention at a dose of 2 12.5 mg/kg/day, are collated in the table below. The reference product used is sodium orthovanadate.

| Compound | Decrease in glycemia (%) | Amount of corresponding vanadium (mg/kg) |
|---|---|---|
| Ex 1 | −45 | 2,50 |
| Ex 5 | −31 | 2,83 |
| Ex 7 | −41 | 1,71 |
| Sodium orthovanadate | −48 | 6,93 |

These results show that the decrease in glycemia observed with the abovementioned compounds is between −31% and −45% for amounts of vanadium 2.5 to 4 times lower than the amount of vanadium corresponding to the administration, under the same conditions, of sodium orthovanadate which causes a decrease in glycemia of −48%.

PHARMACEUTICAL COMPOSITION

EXAMPLE 13: Tablet: preparation formula for 1000 tablets containing a dose of 100 mg

| | |
|---|---|
| Compound of Example 1 | 100 g |
| Hydroxypropyl cellulose | 2 g |
| Wheat starch | 10 g |
| Lactose | 100 g |
| Magnesium stearate | 3 g |
| Talc | 3 g |

We claim:

1. A compound of selected from those formula (I):

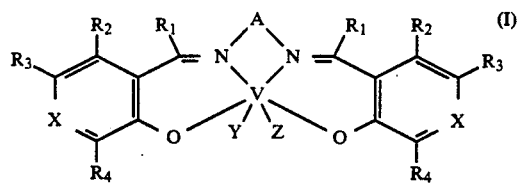

in which:

R$_1$ and R$_4$, which are identical or different, represent hydrogen or linear or branched (C$_1$-C$_6$) alkyl, R$_2$ represents hydrogen, linear or branched (C$_1$-C$_6$) alkyl, hydroxymethyl, —CH$_2$OPO(OH)$_2$ or —CH$_2$OPO(ONa)$_2$, R$_3$ represents hydrogen, linear or branched (C$_1$-C$_6$) alkyl, hydroxyl or any one of the following groups:

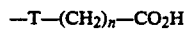

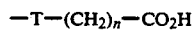

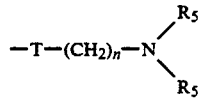

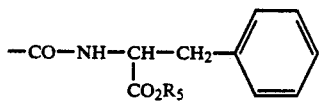

in which:
T represents oxygen or sulfur,
n represents an integer of 1 to 4, inclusive,
$R_5$ represents hydrogen or linear or branched ($C_1$–$C_6$) alkyl,
X represents nitrogen,
represents alkylene of formula —$(CH_2)_p$— in which p represents an integer of 2 to 4, inclusive optionally substituted by one or more linear or branched ($C_1$–$C_4$) alkyl, or any one of the following radicals:

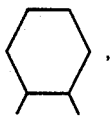 ,  , 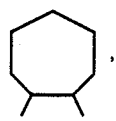 ,

Y and Z together form oxygen, or, alternatively, Y and Z simultaneously represent two hydroxyl groups, and its isomers, as well as its addition salts with a pharmaceutically, acceptable acid or base.

2. A compound of claim 1 which is [N,N'-(bis-pyridoxal)ethylenediimine]oxovanadium (IV), as well as its addition salts with a pharmaceutically-acceptable acid or base.

3. A compound of claim 1 which is [N,N'-bis(5-pyridoxal phosphate)-ethylenediimine]oxovanadium (IV), tetrasodium salt.

4. A compound as claimed in claim 1, wherein A represents ethylene, as well as its addition salts with a pharmaceutically-acceptable acid or base.

5. A compound as claimed in claim 1, wherein Y and Z together form oxygen, as well as its addition salts with a pharmaceutically-acceptable acid or base.

6. A pharmaceutical composition useful for treating diabetes or obesity comprising as active principle an effective amount of a compound as claimed in claim 2 or 3, together with one or more pharmaceutically-acceptable excipients or vehicles.

7. A method for treating an animal or human living body afflicted with diabetes or obesity comprising the step of administering to the living body an amount of a compound of claim 1 which is effective for alleviation of said condition.

8. A pharmaceutical composition useful for treating diabetes or besity method comprising as active principle an affective amount of a compound as claimed in claim 1, together with one or more pharmaceutically-acceptable excipients or vehicles.

9. A method for treating of an animal or human living body afflicted with diabetes or obesity comprising the step of administering to the living body an amount of a compound of claim 2 or 3 which is effective for alleviation of said condition.

* * * * *

UNITED STATES PATENT AND TRADEMARK OFFICE
CERTIFICATE OF CORRECTION

PATENT NO. : 5,278,154

DATED : Jan. 11, 1994

INVENTOR(S) : Jean-Michel Lacoste, Jacques Duhault, Denis Ravel

Page 1 of 2

It is certified that error appears in the above-indentified patent and that said Letters Patent is hereby corrected as shown below:

Title page, [57] ABSTRACT, column 2, line 3; "hydrogenm"
-- should read -- hydrogen --.
Column 1, line 20; "305264 an" should read --305264 and--.
Column 1, approximately line 50; "or group" should read
-- or a group --.
Column 1, approximately line 58; delete "-T-$(CH_2)_n$-$CO_2$H".
Column 2, approximately line 24,25; "or alternatively,"
should read -- or, alternatively --.
Column 2, approximately line 28; 29; "pharmaceutically,
acceptable" should read -- pharmaceutically-acceptable Column 7, line 23, 24; move "3:" from the beginning of line
24 to the end of line 23 and insert after "EXAMPLE".
Column 10, approximately lines 16, 17; move the "9:" from
the beginning of line 17 to the end of line 16 and insert
after "EXAMPLE".
Column 10, approximately lines 51, 52; "for omol of vanadyl tes"
should read --until zero mol of vanadylates --.
Column 12, line 40; "compound of selected from those formula"
should read - compound selected from those of formula --.

Column 12, line 55; "$(OH)_2$ or" should read -- $(OH)_2$, or --.
Column 12, line 56; "move the "$_2$" from the beginning of line 56
to the end of line 55 and insert after "CH".
Column 12, line 58; "hydroxyl or" should read --hydroxyl, or--.

Column 12, approximately line 62; delete the formula.
Column 13, line 15; "represents" should read
-- A represents --.

UNITED STATES PATENT AND TRADEMARK OFFICE
CERTIFICATE OF CORRECTION

PATENT NO. : 5,278,154
DATED : Jan. 11, 1994
INVENTOR(S) : Jean-Michel Lacoste, Jacques Duhault, Denis Ravel It is certified that error appears in the above-indentified patent and that said Letters Patent is hereby corrected as shown below:

Column 13, line 30; "pharmaceutically, acceptable" should read
    -- pharmaceutically-acceptable --.
Column 14, line 23; "or besity method comprising" should read
    -- or obesity comprising --.

Signed and Sealed this

Thirteenth Day of September, 1994

Attest:

BRUCE LEHMAN

Attesting Officer

*Commissioner of Patents and Trademarks*